United States Patent
Clark et al.

(10) Patent No.: US 11,158,402 B2
(45) Date of Patent: Oct. 26, 2021

(54) INTELLIGENT RANKING OF CLINICAL TRIALS FOR A PATIENT

(71) Applicant: International Business Machines Corporation, Armonk, NY (US)

(72) Inventors: Adam Clark, Mantorville, MN (US); Kathryn Lamont Whaley, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 32 days.

(21) Appl. No.: 16/260,382

(22) Filed: Jan. 29, 2019

(65) Prior Publication Data

US 2020/0243168 A1    Jul. 30, 2020

(51) Int. Cl.
*G16H 10/20* (2018.01)
*G16H 40/20* (2018.01)
*G16H 10/60* (2018.01)
*G06N 20/00* (2019.01)
*G16H 50/20* (2018.01)

(52) U.S. Cl.
CPC ............. *G16H 10/20* (2018.01); *G06N 20/00* (2019.01); *G16H 10/60* (2018.01); *G16H 40/20* (2018.01); *G16H 50/20* (2018.01)

(58) Field of Classification Search
CPC ........ G16H 10/20; G16H 10/60; G16H 50/20; G16H 50/70; G16H 20/40; G16H 40/63; G16H 70/20; G16H 50/30; G16H 20/10; G16H 40/20; G06Q 50/24; G06F 40/44; G16B 40/20
See application file for complete search history.

(56) References Cited

U.S. PATENT DOCUMENTS

| | | | |
|---|---|---|---|
| 9,218,584 B2 | 12/2015 | Abraham-Fuchs et al. | |
| 2014/0122113 A1 | 5/2014 | Hoffman, Jr. et al. | |
| 2017/0061102 A1* | 3/2017 | Weber | G06Q 50/01 |
| 2018/0046780 A1 | 2/2018 | Graiver et al. | |
| 2020/0005906 A1* | 1/2020 | Wang | G16H 10/60 |
| 2020/0105380 A1* | 4/2020 | Ennist | G16H 50/30 |

OTHER PUBLICATIONS

He et al, "A Method for Analyzing Commonalities in Clinical Trial Target Populations," AMIA Annu Symp Proc. 2014; 2014: 1777-1786. Published online Nov. 14, 2014.

* cited by examiner

*Primary Examiner* — Maroun P Kanaan
(74) *Attorney, Agent, or Firm* — Patterson + Sheridan, LLP (57) ABSTRACT

Method and apparatus for recommending clinical trials for patients. Embodiments include determining a plurality of clinical trials that a first patient is eligible to participate in. Embodiments further include determining a plurality of current attributes of the first patient. Embodiments further include determining a plurality of predicted attributes of the first patient for a future point in time. Embodiments further include generating a fitness measure for each of the plurality of clinical trials, with respect to the first patient, by processing data about each of the plurality of clinical trials, the plurality of current attributes, and the plurality of predicted attributes with a machine learning (ML) model. Embodiments further include ranking the plurality of clinical trials based on the generated fitness measures.

18 Claims, 5 Drawing Sheets

INTELLIGENT RANKING OF CLINICAL TRIALS FOR A PATIENT

BACKGROUND

The present disclosure relates to using machine learning techniques to deliver clinical trial recommendations, and more specifically, to intelligent ranking of clinical trials based on determined relevance.

Clinical trials in medicine are research studies that are used to test and evaluate various medical treatments, drugs, or devices under development. Typically, clinical trials are defined as a treatment, drug, or device being developed, qualifying criteria (or inclusion criteria) defining the characteristics of patients who may be eligible to participate in a specified trial, and disqualifying criteria defining the characteristics of patients who are not eligible for participation in the trial. For example, the qualifying criteria may include the medical condition that the subject of the clinical trial is addressing, a stage of medical treatment that patients should be at, what previous treatments a patient may have received prior to entering the clinical trial, and the like. The disqualifying criteria defining the characteristics of patients who are not eligible to participate in a specified trial may include, for example, a stage of a disease beyond which a patient would be ineligible for inclusion in the trial, previous treatments that disqualify a patient from participating in the trial, and the like. However, qualifying and disqualifying criteria and other relevant information about clinical trials may sometimes be written in a non-standardized format that cannot easily be cross-compared.

At any given time, a patient may potentially be eligible for participation in a variety of clinical trials. Typically, to determine what clinical trial(s) a patient may be eligible for participation in, the patient's doctors and/or other clinical staff may review the patient's medical records and the qualifying and disqualifying criteria for a number of clinical trials to identify trials that may be of interest to the patient. However, the process of identifying trials that are potentially of interest for the patient may be a time consuming, manual process that requires doctors or other clinical staff to compare potentially voluminous patient records with at least the qualifying and disqualifying criteria for each clinical trial. Further, due to the number and wide variety of clinical trials that may be active at any time, manual searches for trials of interest may miss potentially relevant trials for a given patient. In some cases, manual analysis of potential clinical trials to enroll a patient in may rely on institutional procedures that prioritize clinical trials being run in certain institutions over potentially relevant clinical trials run in other institutions, which may result in potentially relevant clinical trials for a patient being overlooked or otherwise omitted from consideration.

Automated methods for analyzing patient records and clinical trial definitions may not be able to accurately match patients with the clinical trials that patients may be eligible to participate in for various reasons. For example, automated methods may not be able to accurately parse the intent of statements in a clinical trial definition. In another example, automated methods may not be able to understand the implications of a patient's medical records with respect to the ability to successfully complete a clinical trial. In still further examples, automated methods may be unable to determine or identify temporal relationships associated with qualifying or disqualifying criteria for a clinical trial. As such, there is a need in the art for improved techniques for automatically recommending clinical trials for patients.

SUMMARY

According to one embodiment of the present invention, a method includes determining a plurality of clinical trials that a first patient is eligible to participate in; determining a plurality of current attributes of the first patient; determining a plurality of predicted attributes of the first patient for a future point in time; generating a fitness measure for each of the plurality of clinical trials, with respect to the first patient, by processing data about each of the plurality of clinical trials, the plurality of current attributes, and the plurality of predicted attributes with a machine learning (ML) model; and ranking the plurality of clinical trials based on the generated fitness measures. In certain embodiments, a computing system may be configured to perform methods described herein. In some embodiments, a computer-readable storage medium may store instructions that, when executed by one or more processors, cause the one or more processors to perform methods described herein.

DETAILED DESCRIPTION

Embodiments presented herein involve intelligent ranking of clinical trials for a patient using machine learning techniques. One or more machine learning models may be trained using historical clinical trial data and historical patient data in order to output scores for clinical trials based on attributes of a given patient. One or more additional machine learning models may further be trained using historical attributes of patients to predict future attributes of a patient based on current attributes of the patient.

In one example, attributes of historical patients that participated in historical clinical trials are used to train the model(s) to associate certain patient attributes with certain clinical trials. The trained model(s) are then used to determine scores (e.g., relevance or confidence scores) for clinical trials based on current and/or predicted attributes of a given patient (e.g., determined using other trained model(s)). The scores, which may also be referred to as fitness measures, may then be used to rank the clinical trials in an order of relevance to the given patient. As such, techniques described herein allow for accurate and efficient automated identification of clinical trials in which a patient may participate based on a holistic view of the patient's attributes in view of historical attributes of patients that have participated in clinical trials.

Figure 1:
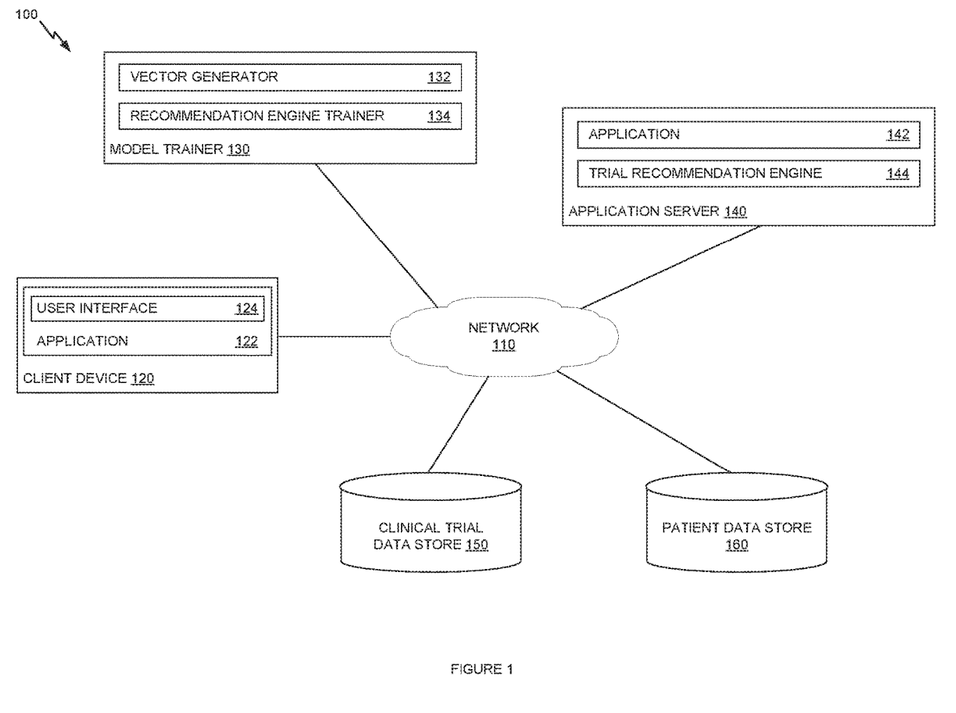
FIG. 1 illustrates an example networked environment in which predictive cognitive models are used to deliver clinical trial recommendations based on patient medical records and clinical trial definitions, according to one embodiment.

FIG. 1 illustrates an example networked computing environment in which predictive models are used to recommend clinical trials for a patient based on patient medical history and clinical trial characteristics. As illustrated, computing environment 100 includes a client device 120, a model trainer 130, an application server 140, a clinical trial data store 150, and a patient data store 160, connected via network 110.

Client device 120 generally is representative of a computing device on which a user can define and/or manage the training of predictive models used by trial recommendation engine 144 to recommend potentially relevant clinical trials for a patient and access application 142 on application server 140 to obtain a set of potentially relevant clinical trials for a patient. Client device 120 may be, for example, a laptop computer, a desktop computer, a thin client, a tablet computer, a mobile computing device, and the like.

Client device 120 includes an application 122 (e.g., a client side component of a client-server application) comprising a user interface 124, which allows a user of client device 120 to interact with a server side component, such as application 142 on application server 140. User interface 122 may, for instance, allow a user of client device 120 to initiate a search for recommended clinical trials that may be of interest to a patient by providing, to application server 140, identifying information of the patient (e.g., the patient name, date of birth, social security number, and/or the like) and/or the patient's medical records (e.g., entered in a standardized format or scanned copies of records that can be processed to determine patient attributes) in a request for one or more potentially relevant clinical trials to present to a patient.

Model trainer 130 generally uses information about patients previously enrolled in trials (e.g., from patient data store 160) and the criteria defined for those trials (e.g., from clinical trial data store 150) to train one or more predictive models used in recommending clinical trials that are potentially relevant to a particular patient. As illustrated, model trainer 130 includes a vector generator 132 and a recommendation engine trainer 134. The training data may include a first set of labeled data used to train the predictive models and a second set of unlabeled data (e.g., for which the intended label is known) used to verify the accuracy of the trained predictive models and to refine the trained predictive models prior to deployment to application server 140.

Vector generator 132 generates a training data set for use by recommendation engine trainer 134 to train a predictive model for recommending potentially relevant clinical trials to a user based on patient medical history (e.g., in the form of patient attributes). To generate the training data set, vector generator 132 can obtain information about previously completed clinical trials from clinical trial data store 150 and patient medical history data from patient data store 160. The information obtained from clinical trial data store 150 may include, for example, a roster of patients enrolled in a specific clinical trial and a definition of that clinical trial. The definition of the clinical trial may include qualifying and disqualifying criteria, patient requirements for participation in the trial, a trial enrollment deadline, and other information defining the clinical trial. The roster of patients may include information identifying each patient that vector generator 132 can use to obtain patient medical records from patient data store 160, information identifying whether each patient successfully completed the trial, and information related to the outcomes of trials for patients.

A training data set may include, for example, a plurality of training data instances that include attributes of patients that participated in particular clinical trials. In some implementations, a training data instance may be in the form of a vector comprising a set of features (e.g., patient attributes such as age, gender, geographic location, medical history, and the like) associated with one or more labels (e.g., an identifier of a clinical trial and/or one or more attributes of the clinical trial).

To generate the training data to be used by recommendation engine trainer 134, vector generator 132 can generate a first set of training data comprising feature data and label data used to train a predictive model and a second set of labeled feature data (e.g., provided as unlabeled data to the predictive model for testing purposes) that can be used to test the generated predictive model. For example, in an embodiment where machine learning models are used to recommend relevant trials for a patient, the first set of data may comprise a plurality of vectors, where the features in each vector include information from patient medical records, and the labels in each vector include the characteristics of a given clinical trial (e.g., identifying information of the given clinical trial and/or qualifying and disqualifying criteria of the given clinical trial). The second set of data may comprise an unlabeled set of patient medical records of patients who have been accepted into a clinical trial, for which the clinical trial is known but excluded from the data set for testing purposes.

In some embodiments, the first set of data may further include additional features that may be used to further refine recommendations of trials that may be relevant to a patient. These additional features may include, for example, information about a current stage of treatment that a patient is in, the specialty of the patient's clinicians, the institution that is treating the patient, and patient completion success for other trials that the patient may have participated in. These additional features may be used to further refine the recommendations delivered by trial recommendation engine 144 to deliver more relevant recommendations to the patient's doctors.

For example, the use of information about a stage of treatment that the patient is in may be used to prioritize recommendations of trials relevant to that particular stage of treatment over trials relevant to earlier or later stages of treatment (e.g., where a patient is in an early stage of a disease, prioritizing clinical trials directed to curative treatments over palliative treatments that are more appropriate for patients with later or terminal stages of the disease). For example, a predictive model may be trained, using the features, to output higher scores when features of a given patient match these features associated with a clinical trial in the training data. Likewise, using information about the patient's clinicians may further indicate, at least implicitly, relevant information about the patient's conditions, such as disease progression, that may be used to prioritize some clinical trials over others (e.g., by assigning higher scores to certain clinical trials). This information may, for example, prioritize clinical trials being held at particular institutions (e.g., based on a distance metric from the patient's clinicians) based on assumptions that patients are more likely to successfully participate in trials that are more easily accessible to the patient. Finally, information about the patient's previous trial completion success may be used as an input to prioritize trials, for example, with similar or less stringent completion requirements to trials that the patient has previously successfully participated in. It should be noted, however, that these additional data points for refining the recommendation of relevant trials are not exhaustive, and other appropriate data points may be used to train predictive models for delivering recommendations of potentially relevant clinical trials for a given user.

Recommendation engine trainer 134 obtains the training data generated by vector generator 132 and, using supervised learning techniques, trains one or more predictive models for delivering recommendations of potentially relevant clinical trials for a patient. Training predictive models may involve using a training data set that includes training inputs that are associated with particular training outputs (e.g., labels). As such, training data comprising historical patient attributes associated with historical clinical trial attributes is used to train one or more predictive models to output scores indicative of strengths of association between a given set of patient attributes and different clinical trials. For example, a trained machine learning model may accept a set of patient attributes as an input and output a set of scores for a plurality of different clinical trials indicating strengths of association between the set of patient attributes and each of the clinical trials.

Predictive models described herein may be, for example, random forest models, and training a prediction model may involve building a "forest" of "trees" representing the training data, where input features are randomly permuted at each split (e.g., each division of the training data). In such embodiments, a prediction model is "trained" by constructing a plurality of decision trees based on sub-divisions of the training data that include random permutations of input features associated with labels.

It is noted that random forest techniques are only included as one example, and that other techniques may be employed for training prediction models. Other types of machine learning models, such as a Naïve Bayes model, logistic regression, decision tree, gradient-boosted tree, multilayer perceptron, and others may also be used as prediction models.

In certain embodiments a single prediction model is used, while in other embodiments a plurality (or ensemble) of prediction models may be used (e.g., for different institutions and/or for different stages of an overall process for recommending clinical trials). In some embodiments, additional attributes may be used to customize a generated prediction model and thus customize the results delivered by the trial recommendation engine 144.

For example, recommendation engine trainer 134 may generate an institutional baseline model using the training data generated by vector generator 132 reflecting institutional preferences for identifying relevant clinical trials for a patient. Individual clinician preferences may then be used to customize the institutional default model to reflect that clinician's preferences in identifying relevant clinical trials (e.g., based on the clinician's previous experiences with clinical trial organizers, interventions that are likely or unlikely to succeed based on prior experience, and the like).

In certain embodiments, predictive models may be trained for predicting future patient attributes based on current patient attributes, and the predicted future patient attributes may be included with current patient attributes as inputs to predictive models for recommending clinical trials.

For instance, a patient may not currently meet a criterion for a clinical trial but a predictive model may be able to predict that the patient will meet the criterion prior to the start of the clinical trial based on historical patient attributes (e.g., other patients with patient data similar to the patient's current patient data went on to meet the criterion within a certain time frame). In one example, a clinical trial requires a patient to have undergone a certain procedure. Historical patient data may indicate that patients with certain attributes (e.g., a medical condition for a certain amount of time) typically undergo the procedure within a particular time frame. This historical patient data may be used to train a predictive model to predict whether a patient will undergo the procedure within a certain time frame based on current attributes of the patient. The output of this predictive model for a given patient may be provided along with other current attributes of the given patient as inputs to a predictive model for recommending clinical trials for the patient. For example, if the value of an attribute is predicted to change prior to the start of the clinical trial, the predicted future value of this attribute may be provided as an input to the predictive model rather than the current value of the attribute. As such, techniques described herein allow for recommending clinical trials not only based on the patient's current attributes, but also based on attributes that the patient is predicted to have in the future.

Application server 140 includes an application 142 and a trial recommendation engine 144. Application 142 may be any type of application in which users can request recommendations of potentially relevant clinical trials for a patient by providing patient data (e.g., identifying information of a patient and/or medical condition information, treatment history, prior clinical trial participation history, and other relevant information) and, in some embodiments, user-defined filters in a search request executed by application 142. Client device 120 may instantiate or initiate a session of application 142 in response to a request for application content (e.g., a list of active clinical trials that are enrolling patients for participation) generated by a user of client device 120. In some embodiments, the instance of a session of application 142 may be instantiated by a user of client device 120 accessing a home page of an application 142 structured as a web application. In other embodiments, user interface 122 may instantiate the instance of application 142 by launching an executable file on client device that includes components that execute locally on client device 120 and use data provided by application 142.

During execution of application 142, a user of client device 120 may request a set of recommended clinical trials for a given patient by providing data related to that patient to application 142 in conjunction with a search request. In response, application 142 provides the received data to trial recommendation engine 144 for analysis. In some embodiments, the user may provide identifying information for a patient (e.g., name, date of birth, social security number, and/or other identifying information), and data for the patient may be retrieved (e.g., by trial recommendation engine 144) from patient data store 160 based on the identifying information. Application 142 may receive a list of potentially relevant clinical trials for the patient ranked in an order of relevance from trial recommendation engine 144, as discussed in further detail below, and display the list of potentially relevant clinical trials in user interface 122 of client device 120. In some embodiments, the list of potentially relevant clinical trials may include a predetermined number of potentially relevant clinical trials for the patient and may be sorted based on the rankings or scores associated with each clinical trial in the list of potentially relevant clinical trials. Application 142 may additionally allow a user of client device 120 to further refine the list of potentially relevant clinical trials using one or more user-defined filters.

Trial recommendation engine 144 uses the prediction model(s) generated by recommendation engine trainer 134, as discussed above, to examine patient data for a given patient and recommend potentially relevant clinical trials for the patient based, at least in part, on the patient's medical history. In some embodiments, trial recommendation engine 144 retrieves patient data, such as medical history, for a given patient from patient data store 160 based on identifying information of the patient (e.g., received from a user of client device 120). Patient data may include a plurality of different types of patient attributes, such as aspects of the given patient's medical history. Patient attributes may, in some embodiments, include scheduled events that have not yet occurred (e.g., medical procedures scheduled for future dates).

In some embodiments, trial recommendation engine 144 first determines a plurality of clinical trials for which the given patient is eligible based on qualifying criteria and disqualifying criteria for clinical trials (e.g., retrieved from clinical trial data store 150), such as evaluating the qualifying criteria and disqualifying criteria based on the patient attributes. In certain embodiments, trial recommendation engine 144 predicts future attributes of the given patient, such as by providing certain current attributes of the patient (e.g., retrieved from patient data store 160) as inputs to one or more predictive models that output predicted future attributes.

Trial recommendation engine 144 provides patient attributes, which may include current and predicted future attributes, of the given patient as inputs to one or more predictive models for recommending clinical trials (with scores) for the given patient. In some embodiments, trial recommendation engine 144 also provides identifying information of the clinical trials for which the given patient is eligible as inputs so that the predictive model(s) only determine scores for those particular clinical trials. For example, in one embodiment a predictive model accepts patient attributes as inputs and outputs a score for every clinical trial for which the predictive model was trained, while in another embodiment a predictive model accepts both patient attributes and identifiers of clinical trials as inputs and outputs scores only for the clinical trials identified in the inputs.

For example, a predictive model may process the inputs and output a score for each of a plurality of clinical trials (e.g., identified by trial recommendation engine 144), each score indicating a strength of relevance of a respective clinical trial to the given patient. In certain embodiments, predictive models may be trained based on individual clinician preferences for a clinician that requested the recommended clinical trials, and outputs of the predictive models may be in accord with the clinician preferences (e.g., clinical trials of a type preferred by the clinician may be assigned higher scores according to the training of the model). Techniques described herein may involve fuzzy logic, as output scores are not only based on bright-line rules (e.g., whether or not a patient meets a criterion for a clinical trial), but are based on degrees of association (e.g., the patient may not meet a certain criterion or attribute that is historically associated with a clinical trial explicitly, but may be within a threshold distance and/or may be predicted to meet the criterion or attribute prior to the time of the clinical trial). Predictive models, therefore, are a means of implementing fuzzy logic. Fuzzy logic may also be employed in determining which clinical trials a patient is eligible for (e.g., as a first step before providing patient attributes and identifying information of the clinical trials for which the patient is eligible as inputs to a predictive model).

In some embodiments, trial recommendation engine 144 may rank the plurality of clinical trials based on the scores output by the predictive model(s). Trial recommendation engine 144 may further filter the clinical trials, such as based on user input (e.g., filters and/or preferences provided by the user via user interface 122). In some embodiments, trial recommendation engine 144 also applies certain bright-line rules in order to filter the clinical trials, such as to prevent recommending a clinical trial with a low score to a user when the clinical trial would in fact not be appropriate for the user at all. For example, if a clinical trial is only for HER-2 negative patients and the given patient is HER-2 positive, then the clinical trial may be filtered out of the list of clinical trials provided to the user.

Trial recommendation engine 144 provides a ranked list of clinical trials to application 142, which may provide the ranked list to user interface 122 for display to the user. In certain embodiments, trial recommendation engine 144 provides information to application 142 regarding attributes that were predicted so that this information can be provided to the user. For example, if trial recommendation engine 144 recommends a certain clinical trial based on a prediction that the given patient will undergo a certain procedure in the future, then the user may be informed that the clinical trial is only recommended if the prediction turns out to be accurate.

Clinical trial data store 150 may be a data storage entity, such as a database or repository, that stores data about clinical trials. For example, clinical trial data store 150 may store qualifying and disqualifying criteria for clinical trials, rosters of patients that participated in clinical trials, information about outcomes of clinical trials, and the like. For example, the data in clinical trial data store 150 may have been entered by one or more users (e.g., clinicians or professionals), or may have been mined from various sources, such as articles and reports related to clinical trials.

Patient data store 160 may be a data storage entity, such as a database or repository, that stores data about patients. For example, patient data store 160 may store personal data, patient attributes, medical records, patient preferences, and other data related to patients, which may have been provided by one or more users, such as patients and/or clinicians.

While model trainer 130, application server 140, clinical trial data store 150, and patient data store 160 are illustrated as separate components in FIG. 1, it should be recognized that model trainer 130, application server 140, clinical trial data store 150, and patient data store 160 may be implemented on any number of computing systems, either as one or more standalone systems or in a distributed environment.

Figure 2:
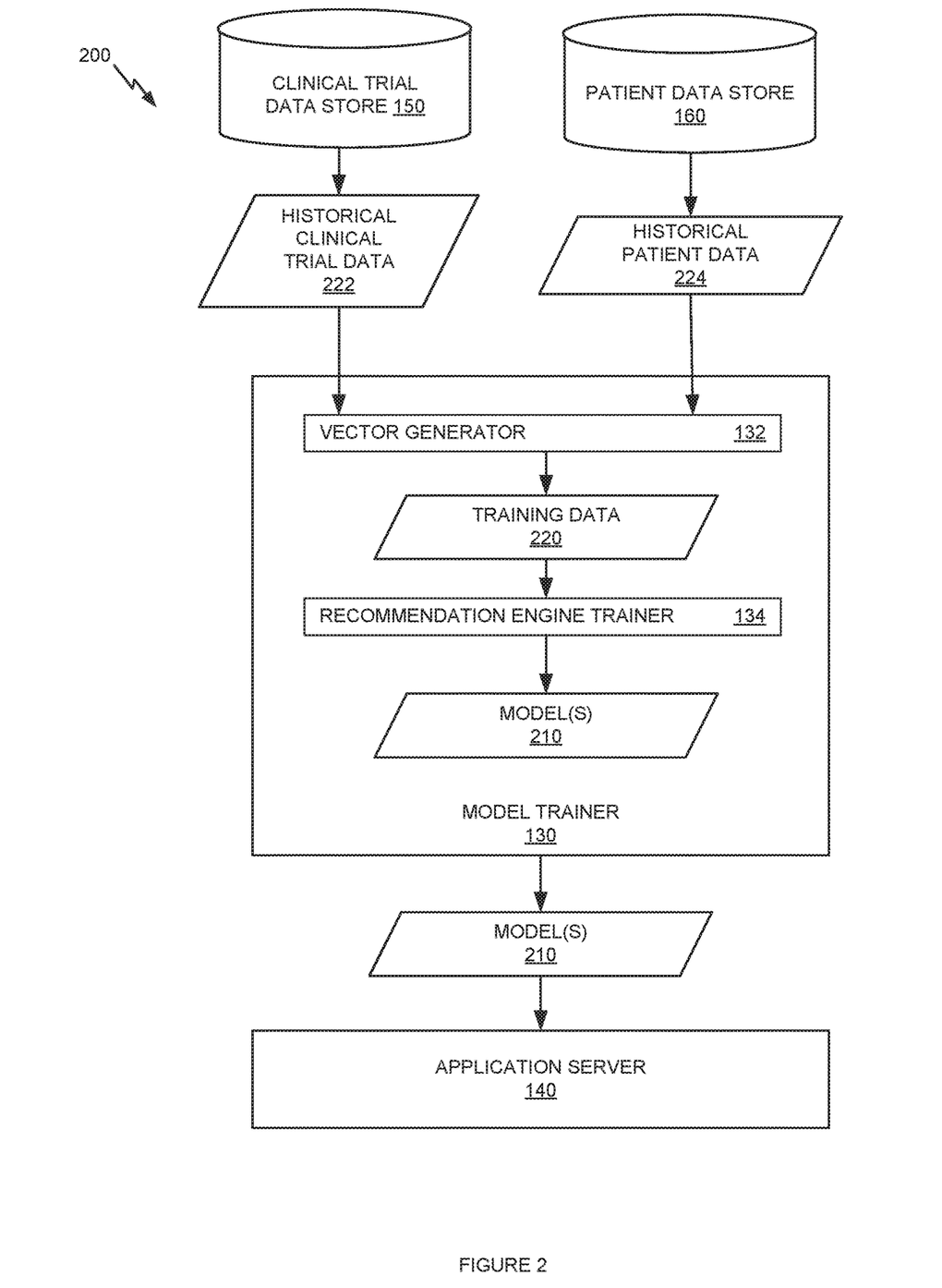
FIG. 2 illustrates an example of training predictive models for recommending clinical trials to patients.

FIG. 2 illustrates an example 200 of training predictive models for recommending clinical trials to patients. Example 200 includes model trainer 130 (comprising vector generator 132 and recommendation engine trainer 134), clinical trial data store 150, patient data store 160, and application server 140 of FIG. 1.

Model trainer 130 retrieves historical clinical trial data 222 from clinical trial data store 150 and historical patient data 224 from patient data store 160. Historical clinical trial data 222 may include information regarding qualifying and disqualifying criteria for a plurality of clinical trials. Historical clinical trial data 222 may also include lists of patients (e.g., identified using information such as names, dates of birth, and social security numbers) that participated in historical clinical trials.

Historical patient data 224 may include attributes of patients that participated in historical clinical trials (e.g., retrieved based on identifying information of the patients included in historical clinical trial data 222), such as medical history of the patients.

Vector generator 132 uses historical clinical trial data 222 and historical patient data 224 to generate training data 220 for generating one or more trained models 210. For example, training data 220 may include a plurality of training data instances (e.g., vectors) associating historical patient attributes with characteristics of clinical trials. Training data 220 is provided to recommendation engine trainer 134, which uses training data 220 to generate one or more trained models 210, such as using various supervised machine learning concepts. One or more of models 210 may be trained to output scores for clinical trials based on input patient attributes, while other models 210 may be trained to predict future attributes of a patient based on current patient attributes. In some embodiments, one or more of models 210 are trained based on specific clinician preferences and are used to recommend clinical trials for patients when requested by certain clinicians. For example, training data 220 may further include data related to clinician preferences, and the clinician preferences may be used to adjust the weights of features within the models.

Model trainer 130 provides the one or more models 210 to application server 140, which loads the one or more models 210 into memory for use in recommending clinical trials for patients.

Figure 3:
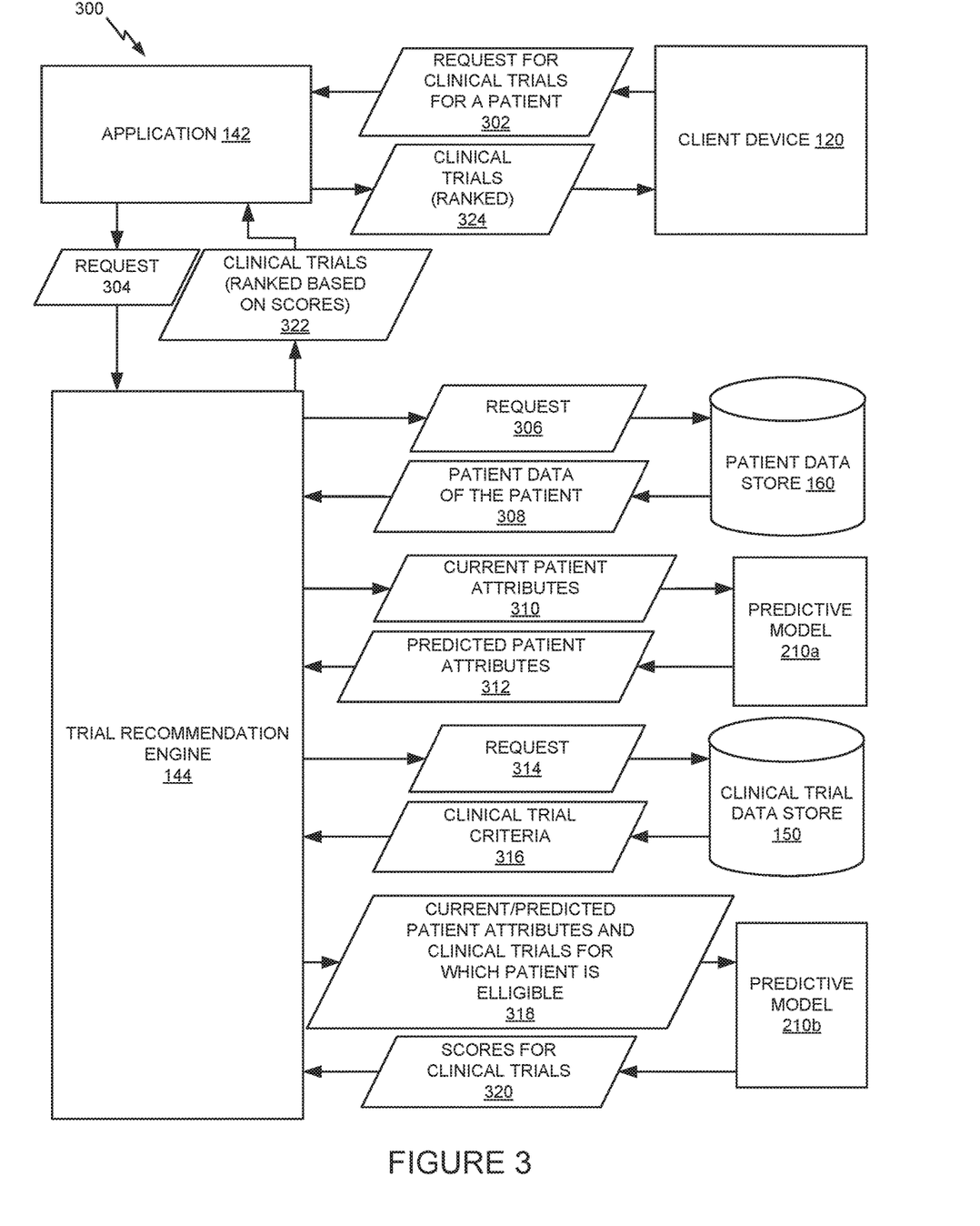
FIG. 3 illustrates an example of using trained predictive models to intelligently rank recommended clinical trials for patients.

FIG. 3 illustrates an example 300 of using trained predictive models to rank recommended clinical trials for patients. Example 300 includes client device 120, application 142, trial recommendation engine 144, patient data store 160, and clinical trial data store 150 of FIG. 1. Example 300 also includes predictive models 210a and 210b, which may be models 210, trained as illustrated in example 200 of FIG. 2. In example 300, predictive model 210a is trained to predict future patient attributes based on current patient attributes and predictive model 210b is trained to output scores for clinical trials in response to inputs comprising patient attributes and identifying information of clinical trials for which the patient is eligible.

Client device 120 sends a request 302 for clinical trials for a patient to application 142. For example, a user may have initiated a request for clinical trials for the patient via a user interface of client device 120. Request 302 may include identifying information of the patient. Application 142 sends a request 304 to trial recommendation engine 144 based on request 302, such as including the identifying information of the patient.

Trial recommendation engine 144 sends a request 306 to patient data store 160 for patient data related to the patient identified in requests 302 and 304. Patient data store 160 provides patient data 308 of the patient to trial recommendation engine 144 in response to request 306. Patient data 308 may, for instance, include patient attributes such as aspects of the patient's medical history (e.g., diagnoses, procedures, allergies, medications, family medical history, and the like).

Trial recommendation engine 144 provides current patient attributes 310 (e.g., from patient data 308) as inputs to predictive model 210a, which outputs predicted patient attributes 312, which may include one or more predicted values of patient attributes at one or more future points (e.g., at particular intervals).

Trial recommendation engine 144 then sends a request 314 to clinical trial data store for clinical trial criteria 316, which may comprise qualifying and disqualifying criteria of a plurality of clinical trials (e.g., all clinical trials for which criteria are store in clinical trial data store 150). Trial recommendation engine 144 determines which clinical trials the patient may be eligible for by determining whether the patient meets the qualifying criteria and/or disqualifying criteria (e.g., exactly or within a certain threshold distance using fuzzy logic) based on patient data 308 and, in some embodiments, based on predicted patient attributes 312. As such, trial recommendation engine 144 determines the set of clinical trials for which the patient is eligible.

Trial recommendation engine 144 then provides inputs 318 to predictive model 210b, including current patient attributes determined from patient data 308, predicted patient attributes 312, and identifying information of the clinical trials for which the patient is eligible. In some embodiments, patient attributes 310 are provided directly as inputs to a model 210, which outputs scores 320 for clinical trials (e.g., the clinical trials identified in inputs 318) for the patient. The scores 320 may, for example, be output in the form of a set of value pairs, each pair including an identifier of a clinical trial and a score indicating a strength of relevance (e.g., a fitness measure) of the clinical trial with respect to the patient.

Trial recommendation engine 144 receives the scores 320 output by predictive model 210b and ranks the clinical trials based on the scores. Trial recommendation engine 144 may also apply one or more filters and/or rules to the clinical trials in order to further refine the list. Trial recommendation engine 144 then provides the ranked clinical trials 322 to application 142 in response to request 304. Application 142 provides the ranked clinical trials 324 received at 322 to client device 120 for display to the user in response to request 302. For example, client device 120 may display the ranked clinical trials 324 via a user interface that lists clinical trials likely to be relevant to the patient.

While example 300 depicts ranking of clinical trials for a single patient, it is noted that techniques described herein may also be used to rank clinical trials for a plurality of patients, such as in response to a request from a clinician.

Figure 4:
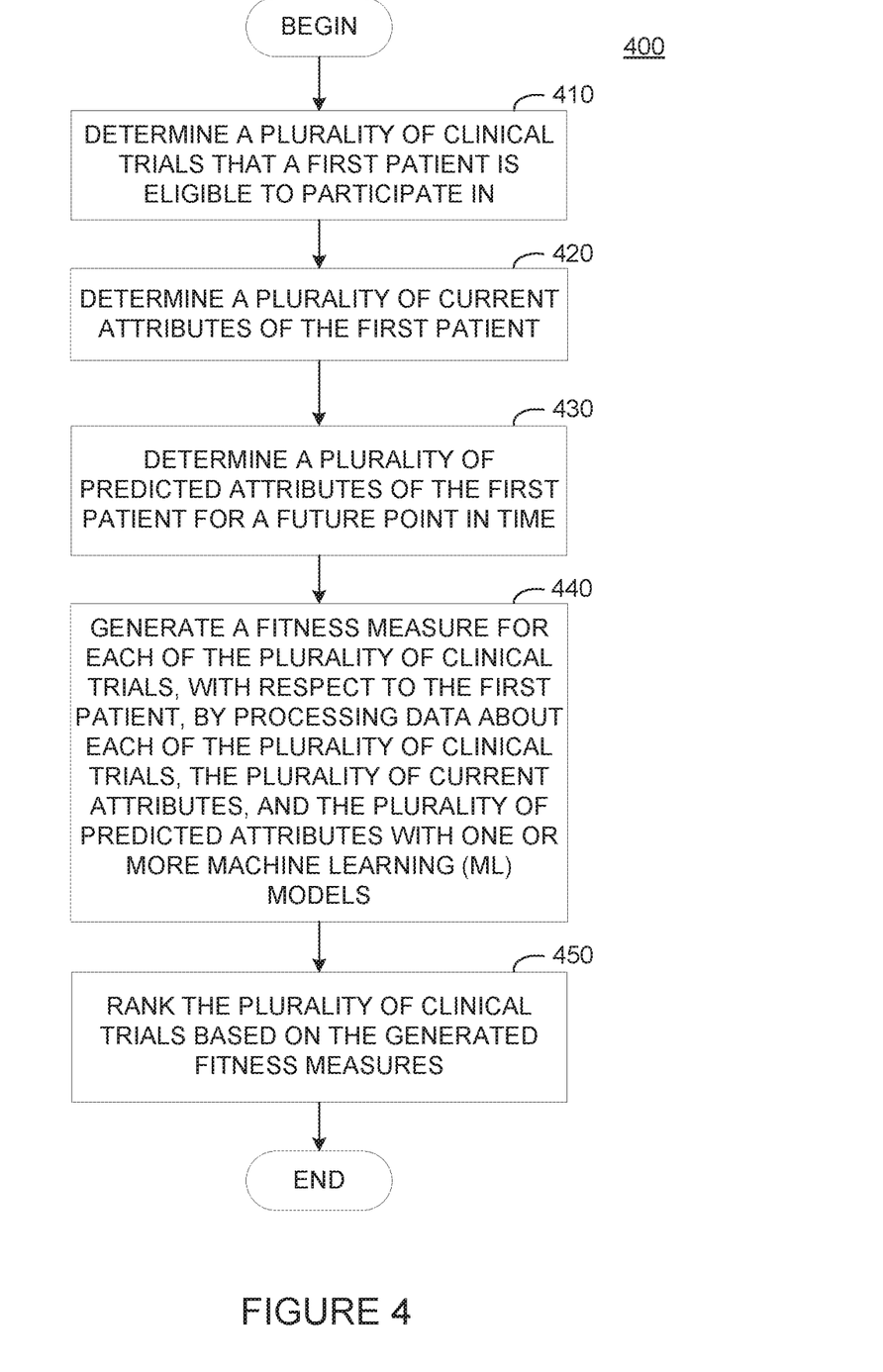
FIG. 4 illustrates example operations for intelligently ranking recommended clinical trials for patients.

FIG. 4 illustrates example operations 400 for ranking recommended clinical trials for patients. For example, operations 400 may be performed by trial recommendation engine 144 of FIGS. 1 and 3.

At step 410, a plurality of clinical trials that a first patient is eligible to participate in is determined. For example, a user of a client device may have requested a list of clinical trial relevant to the first patient, and the first patient may have been identified in the request, such as by identifying information of the first patient. The determined plurality of clinical trials may include all clinical trials that the first patient is eligible to participate in, such as based on qualifying criteria of the plurality of clinical trials and attributes of the first patient retrieved using the identifying information of the first patient. It is noted that, at step 410, fuzzy logic may be employed so that if the first patient almost meets an qualifying criterion of a clinical trial (e.g., within a certain threshold) the first patient may be considered to be eligible for the clinical trial. Eligibility may also include one or more bright-line rules such that if the first patient does not meet a bright-line rule, the patient is considered ineligible.

At step 420, a plurality of current attributes of the first patient is determined. For example, trial recommendation engine 144 of FIG. 1 may retrieve the plurality of current attributes of the first patient from patient data store 160 of FIG. 1, such as using identifying information of the first patient that was included in a request from a client device.

At step 430, a plurality of predicted attributes of the first patient for a future point in time is determined. For example, trial recommendation engine 144 of FIG. 1 may provide one or more current attributes of the first patient determined at step 420 as inputs to one or more trained predictive models, and the one or more trained predictive models may output the plurality of predicted attributes of the first patient based on the inputs.

At step 440, a fitness measure for each of the plurality of clinical trials is determined with respect to the first patient by processing data about each of the plurality of clinical trials, the plurality of current attributes, and the plurality of predicted attributes with one or more machine learning models (e.g., predictive models). For example, trial recommendation engine 144 of FIG. 1 may provide the plurality of current attributes and the plurality of predicted attributes as inputs (e.g., along with identifying information of the plurality of clinical trials) to one or more of models 210 of FIGS. 2 and 3, which may have been trained as described with respect to example 200 of FIG. 2. The one or more machine learning models may output a score for each of plurality of clinical trials indicating a degree of relevance (e.g., fitness measure) between the first patient and a respective clinical trial.

At step 450, the plurality of clinical trials is ranked based on the generated fitness measures (e.g., based on the scores). For example, trial recommendation engine 144 of FIG. 1 may rank the plurality of clinical trials by score from highest to lowest. In some embodiments, trial recommendation engine 144 of FIG. 1 provides the ranked clinical trials to a client device for display to a user, such as via a graphical user interface.

Figure 5:
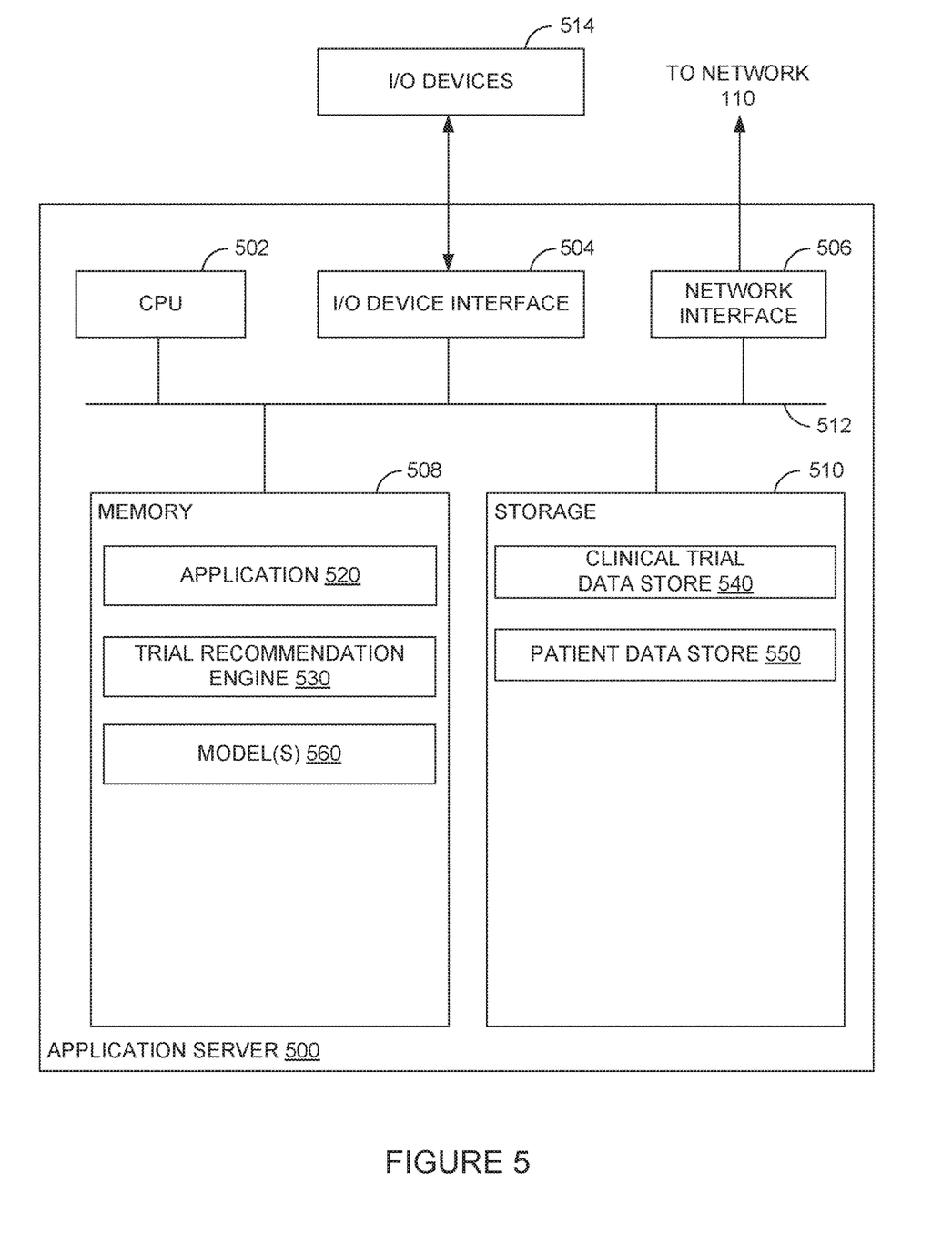
FIG. 5 illustrates an example system in which aspects of the present disclosure may be performed.

FIG. 5 depicts a computing system 500 with which embodiments of the present disclosure may be implemented. For example, computing system 500 may represent application server 140 of FIG. 1.

System 500 includes a central processing unit (CPU) 502, one or more I/O device interfaces 504 (that may provide connections for various I/O devices 514, such as keyboards, displays, mouse devices, and the like) to the system 500, network interface 506 (e.g., a physical network interface card), memory 508, storage 510, and an interconnect 512. It is noted that one or more components of system 500 may alternatively be located remotely and accessed via a network, such as network 110. It is further contemplated that one or more components of system 500 may comprise physical or virtualized components.

CPU 502 may receive and execute instructions stored in memory 508. Similarly, the CPU 502 may receive and store data related to applications in memory 508. The interconnect 512 transmits programming instructions and application data, among the CPU 502, I/O device interface 504, network interface 506, memory 508, and storage 510. CPU 502 is included to be representative of a single CPU, multiple CPUs, a single CPU having multiple processing cores, and other arrangements.

Additionally, the memory 508 may represent a random access memory. Storage 510 may be a disk drive, solid state drive, or a collection of storage devices distributed across multiple storage systems. Although shown as a single unit, the storage 510 may be a combination of fixed and/or removable storage devices, such as fixed disc drives, removable memory cards or optical storage, network attached storage (NAS), or a storage area-network (SAN).

Storage 510 comprises clinical trial data store 540 and patient data store 550, which are representative of clinical trial data store 150 and patient data store 160 of FIG. 1. As shown, memory 508 includes application 520, trial recommendation engine 530, and model(s) 560, which are representative of application 142 and trial recommendation engine 144 of FIG. 1 and model(s) 210 of FIG. 2.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Reference is made herein to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim (s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., application 142 and/or trial recommendation engine 144 of FIG. 1) or related data available in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A computer-implemented method comprising:
  determining a plurality of clinical trials that a first patient is eligible to participate in;
  determining a plurality of current attributes of the first patient;
  determining a plurality of predicted attributes of the first patient for a future point in time;
  providing inputs to a machine learning (ML) model based on the plurality of current attributes of the first patient, the plurality of predicted attributes of the first patient, and the plurality of clinical trials, wherein the ML model has been trained through a supervised learning process comprising:
generating a training data set comprising historical patient attributes associated with labels comprising characteristics of historical clinical trials; and
using the training data set to train the ML model to output fitness measures indicating strengths of association between given sets of patient attributes and given clinical trials associated with the characteristics;
receiving outputs from the ML model in response to the inputs, the outputs comprising a respective fitness measure for each respective clinical trial of the plurality of clinical trials, with respect to the first patient; and
ranking the plurality of clinical trials based on the outputs from the ML model.

2. The computer-implemented method of claim 1, wherein determining the plurality of predicted attributes comprises:
identifying a plurality of patients that are clinically similar to the first patient;
determining, for each respective patient of the plurality of patients, a respective progression of a first disorder; and
determining a predicted progression of the first disorder for the first patient, based on the respective progressions for the plurality of patients.

3. The computer-implemented method of claim 1, wherein determining the plurality of current attributes of the first patient comprises:
determining a treatment history of the first patient; and
determining whether the treatment history of the first patient includes one or more unexpected events.

4. The computer-implemented method of claim 1, wherein determining the plurality of current attributes of the first patient comprises, for each respective clinical trial of the plurality of clinical trials:
determining a respective treatment to be used in the respective clinical trial; and
determining whether the first patient has already undergone the respective treatment.

5. The computer-implemented method of claim 1, wherein the ML model is trained in part by:
identifying a corpus of prior trials;
determining a relative importance of a plurality of attributes for each of the prior trials in the corpus of prior trials; and
training the ML model based on the relative importance of the plurality of attributes.

6. The computer-implemented method of claim 1, the method further comprising: upon determining that a fitness measure of a first trial of the plurality of clinical trials is below a predefined threshold, indicating that the first patient is not eligible for the first trial.

7. A system, comprising one or more processors and a computer-readable storage medium having computer-readable program code embodied therewith, the computer-readable program code executable by the one or more computer processors to perform a method, the method comprising:
determining a plurality of clinical trials that a first patient is eligible to participate in;
determining a plurality of current attributes of the first patient;
determining a plurality of predicted attributes of the first patient for a future point in time;
providing inputs to a machine learning (ML) model based on the plurality of current attributes of the first patient, the plurality of predicted attributes of the first patient, and the plurality of clinical trials, wherein the ML model has been trained through a supervised learning process comprising:
generating a training data set comprising historical patient attributes associated with labels comprising characteristics of historical clinical trials; and
using the training data set to train the ML model to output fitness measures indicating strengths of association between given sets of patient attributes and given clinical trials associated with the characteristics;
receiving outputs from the ML model in response to the inputs, the outputs comprising a respective fitness measure for each respective clinical trial of the plurality of clinical trials, with respect to the first patient; and
ranking the plurality of clinical trials based on the outputs from the ML model.

8. The system of claim 7, wherein determining the plurality of predicted attributes comprises:
identifying a plurality of patients that are clinically similar to the first patient;
determining, for each respective patient of the plurality of patients, a respective progression of a first disorder; and
determining a predicted progression of the first disorder for the first patient, based on the respective progressions for the plurality of patients.

9. The system of claim 7, wherein determining the plurality of current attributes of the first patient comprises:
determining a treatment history of the first patient; and
determining whether the treatment history of the first patient includes one or more unexpected events.

10. The system of claim 7, wherein determining the plurality of current attributes of the first patient comprises, for each respective clinical trial of the plurality of clinical trials:
determining a respective treatment to be used in the respective clinical trial; and
determining whether the first patient has already undergone the respective treatment.

11. The system of claim 7, wherein the ML model is trained in part by:
identifying a corpus of prior trials;
determining a relative importance of a plurality of attributes for each of the prior trials in the corpus of prior trials; and
training the ML model based on the relative importance of the plurality of attributes.

12. The system of claim 7, the method further comprising:
upon determining that a fitness measure of a first trial of the plurality of clinical trials is below a predefined threshold, indicating that the first patient is not eligible for the first trial.

13. A computer-readable storage medium having computer-readable program code embodied therewith, the computer-readable program code executable by one or more computer processors to perform a method, the method comprising:
determining a plurality of clinical trials that a first patient is eligible to participate in;
determining a plurality of current attributes of the first patient;
determining a plurality of predicted attributes of the first patient for a future point in time;
providing inputs to a machine learning (ML) model based on the plurality of current attributes of the first patient, the plurality of predicted attributes of the first patient, and the plurality of clinical trials, wherein the ML model has been trained through a supervised learning process comprising:
- generating a training data set comprising historical patient attributes associated with labels comprising characteristics of historical clinical trials; and
- using the training data set to train the ML model to output fitness measures indicating strengths of association between given sets of patient attributes and given clinical trials associated with the characteristics;

receiving outputs from the ML model in response to the inputs, the outputs comprising a respective fitness measure for each respective clinical trial of the plurality of clinical trials, with respect to the first patient; and ranking the plurality of clinical trials based on the outputs from the ML model.

14. The computer-readable storage medium of claim 13, wherein determining the plurality of predicted attributes comprises:
- identifying a plurality of patients that are clinically similar to the first patient;
- determining, for each respective patient of the plurality of patients, a respective progression of a first disorder; and
- determining a predicted progression of the first disorder for the first patient, based on the respective progressions for the plurality of patients.

15. The computer-readable storage medium of claim 13, wherein determining the plurality of current attributes of the first patient comprises:
- determining a treatment history of the first patient; and
- determining whether the treatment history of the first patient includes one or more unexpected events.

16. The computer-readable storage medium of claim 13, wherein determining the plurality of current attributes of the first patient comprises, for each respective clinical trial of the plurality of clinical trials:
- determining a respective treatment to be used in the respective clinical trial; and
- determining whether the first patient has already undergone the respective treatment.

17. The computer-readable storage medium of claim 13, wherein the ML model is trained in part by:
- identifying a corpus of prior trials;
- determining a relative importance of a plurality of attributes for each of the prior trials in the corpus of prior trials; and
- training the ML model based on the relative importance of the plurality of attributes.

18. The computer-readable storage medium of claim 13, the method further comprising: upon determining that a fitness measure of a first trial of the plurality of clinical trials is below a predefined threshold, indicating that the first patient is not eligible for the first trial.

* * * * *